United States Patent [19]

Kumobayashi et al.

[11] Patent Number: 5,128,489
[45] Date of Patent: Jul. 7, 1992

[54] PROCESS FOR PRODUCTION OF OPTICALLY ACTIVE 2-(TETRAHYDROPYRAN-2-YLOXY)-1-PROPANOL

[75] Inventors: Hidenori Kumobayashi; Akio Tachikawa; Yoshiki Okeda; Toshihiro Fujiwara, all of Kanagawa, Japan

[73] Assignees: Takasago International Corporation; Daiichi Pharmaceutical Co., Ltd., both of Tokyo, Japan

[21] Appl. No.: 592,752

[22] Filed: Oct. 4, 1990

[30] Foreign Application Priority Data

Oct. 5, 1989 [JP] Japan .................................. 1-261031

[51] Int. Cl.⁵ .......................................... C07D 309/12
[52] U.S. Cl. ...................................... 549/419; 549/423
[58] Field of Search ............................ 549/423, 419

[56] References Cited

U.S. PATENT DOCUMENTS 3,989,728 11/1976 Martin ............................ 260/410.7

FOREIGN PATENT DOCUMENTS 0322815 7/1989 European Pat. Off. .
03022090 1/1988 Japan ................................. 549/423

*Primary Examiner*—Jane T. Fan
*Assistant Examiner*—Amelia A. Owens
*Attorney, Agent, or Firm*—Sughrue, Mion, Zinn, Macpeak & Seas

[57] ABSTRACT

A process for production of an optically active isomer of 2-(tetrahydropyran-2-yloxy)-1-propanol represented by formula (I):

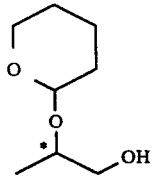

(I)

is disclosed, which comprises reacting an optically active isomer of a 1-acyloxy-2-propanol represented by formula (II):

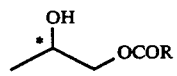

(II)

wherein R is a substituted or unsubstituted aryl group, with 3,4-dihydro-2H-pyran to obtain an optically active isomer of a 1-acyloxy-2-(tetrahydropyran-2-yloxy)propane represented by formula (III):

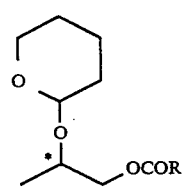

(III)

wherein R is as defined above, and hydrolyzing the compound (III) to eliminate the acyl group. The optically active isomer of 2-(tetrahydropyran-2-yloxy)-1-propanol represented by formula (I) is an intermediate for synthesis of pyridobenzoxazine derivatives useful as a synthetic antibacterial agent, particularly an optically active isomer of ofloxacin.

4 Claims, No Drawings

PROCESS FOR PRODUCTION OF OPTICALLY ACTIVE 2-(TETRAHYDROPYRAN-2-YLOXY)-1-PROPANOL

FIELD OF THE INVENTION

This invention relates to a novel process for production of optically active 2-(tetrahydropyran-2-yloxy)-1-propanol which is an intermediate for synthesis of pyridobenzoxazine derivatives useful as a synthetic antibacterial agent, particularly an optically active isomer of ofloxacin. This invention also relates to acyl derivatives of 2-(tetrahydropyran-2-yloxy)-1-propanol and to a process for production of the same.

BACKGROUND OF THE INVENTION

Ofloxacin is known as a quinolone series synthetic antibacterial agent having a wide antibacterial spectrum and high safety. Ofloxacin, as shown from its chemical structure, has an asymmetric carbon atom at the 3-position of the oxazine ring and includes two enantiomers, i.e., (R) isomer, and (S) isomer. In comparison of antibacterial activity between the (R) isomer and the (S) isomer, the antibacterial activity of the (S) isomer is 8 to 128 times that of the (R) isomer and, what is more, the (S) isomer is less toxic than the (R) isomer. Accordingly, the (S) isomer of ofloxacin, i.e., 3-(S)-9fluro-2,3-dihydro-3-methyl-10-(4-methyl-1-piperazinyl)-7-oxo-7H-pyrido[1,2,3-de]-1,4-benzoxazine-6-carboxylic acid, is especially useful as a synthetic antibacterial agent (*Farumashia*, 25, 322 (1989)).

The present inventors studied a method for the production of the (S) isomer of ofloxacin. As a result, they found a method wherein optically active 2-(tetrahydropyran-2-yloxy)-1-propanol is used as an intermediate and applied a patent application (JP-A-2-732; the term "JP-A" as used herein means as an "unexamined published Japanese patent application").

As a method for producing optically active 2-(tetrahydropyran-2-yloxy)-1-propanol, there is known a method in which optically active lactic acid or an ester thereof as a raw material is reacted with 3,4-dihydro-2H-pyran in the presence of an acid catalyst, to form an optically active 2-(tetrahydropyran-2-yloxy)propionic acid ester which is then reduced with lithium aluminum hydride (Robert G. Ghirardelli, *J. Am. Chem. Soc.*, 95, 4987(1973)).

However, not only is an (R)-lactic acid ester which is required for producing 2-(R)-(tetrahydropyran-2-yloxy)-1-propanol as an intermediate for synthesis of the (S) isomer of ofloxacin according to the method disclosed in the above-cited literature more expensive than an optically active (S) lactic acid ester, but lithium aluminum hydride used as the reducing agent is also expensive.

Accordingly, development of an economically and industrially useful, novel process for production of 2-(R)-(tetrahydropyran-2-yloxy)-1-propanol has been keenly demanded.

In the light of the situation described above, the present inventors have studied how to solve the above-mentioned drawbacks. As a result, it has been found that optically active 2-(tetrahydropyran-2-yloxy)-1-propanol having high optical purity can be obtained commercially advantageously by the use of an easily available, optically active 1-acyloxy-2-propanol through a simple operation, leading to accomplishment of the present invention.

SUMMARY OF THE INVENTION

That is, an object of this invention is to provide a process for production of an optically active isomer of 2-(tetrahydropyran-2-yloxy)-1-propanol represented by formula (I):

which comprises reacting an optically active isomer of a 1-acyloxy-2-propanol represented by formula (II):

wherein R is a substituted or unsubstituted aryl group, with dihydropyran to obtain an optically active isomer of a 1-acyloxy-2-(tetrahydropyran-2-yloxy)propane represented by formula (III):

wherein R is as defined above, and hydrolyzing the compound (III) to eliminate the acyl group.

Another object of the present invention is to provide a compound represented by formula (III) which is useful as an intermediate for synthesis of an optically active isomer of 2-(tetrahydropyran-2-yloxy)-1-propanol represented by formula (I).

A further object of the present invention is to provide a process for production of a compound represented by formula (III).

DETAILED DESCRIPTION OF THE INVENTION

In formulae (I) and (III), the absolute configuration in the 2-position is either an (R)-form or an (S)-form, while the absolute configuration in the 2-position of the pyranyl moiety is not specifically limited.

The process of this invention is performed according to the following reaction scheme:

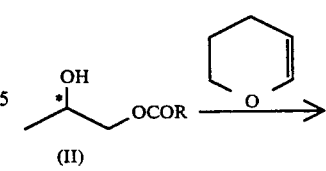

-continued

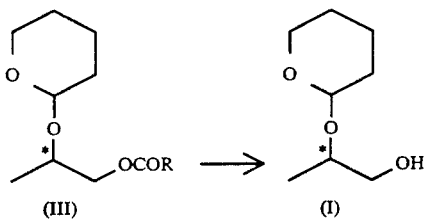

wherein R is as defined above.

First of all, the reaction between the optically active isomer of 1-acyloxy-2-propanol (II) and 3,4-dihydro-2H-pyran is preferably carried out, for example, in the presence of an acid catalyst in a suitable solvent or in the absence of any solvent. Examples of acid catalysts to be used include hydrochloric acid, sulfuric acid, camphor-10-sulfonic acid, p-toluenesulfonic acid, a pyridine salt of p-toluenesulfonic acid, methanesulfonic acid, and a pyridine salt of methanesulfonic acid. Examples of solvents to be used include toluene, chlorobenzene, dichloromethane, dichloroethane, tetrahydrofuran, and diisopropyl ether. The reaction temperature is preferably from −10° C. to 25° C., especially from 5° C. to 15° C., and the reaction time is preferably from 1 to 10 hours, especially from 2 to 4 hours.

So far as the present inventors know, the thus obtained 1-acyloxy-2-(tetrahydropyran-2-yloxy)propane of formula (III) is a novel compound which has not yet been described in any published literature. In formula (III), examples of the substituted or unsubstituted aryl group represented by R include a phenyl group which may have one or two or more substituent groups selected from a nitro group and a halogen atom, such as a phenyl group, a p-nitrophenyl group, a m-nitrophenyl group, an o-nitrophenyl group, a 2,4-dinitrophenyl group, a 2,6-dinitrophenyl group, a 3,4-dinitrophenyl group, a 3,5-dinitrophenyl group, a p-bromophenyl group, a m-bromophenyl group, an o-bromophenyl group, a p-iodophenyl group, a m-iodophenyl group, an o-iodophenyl group, a p-chlorophenyl group, a m-chlorophenyl group, and an o-chlorophenyl group, with a p-nitrophenyl group and a p-bromophenyl group being preferred.

The hydrolysis of the 1-acyloxy-2-(tetrahydropyran-2-yloxy)propane of formula (III) is preferably carried out by usual hydrolysis in, for example, a mixed solution of methanol and potassium hydroxide or an aqueous potassium hydroxide solution. The reaction is usually completed at from 0° C. to 25° C. for from one to 5 hours.

The thus obtained optically active 2-(tetrahydropyran-2-yloxy)-1-propanol of formula (I) can be readily isolated by, for example, extraction with an organic solvent such as dichloromethane or dichloroethane and distillation in vacuo.

The acyloxy-2-propanol of formula (II) to be used as one of the starting materials can be produced by, for example reacting an optically active isomer of 1,2-propanediol with an acid halide represented by formula (V):

RCOX    (V)

wherein X is a halogen atom, and R is as defined above.

The optically active isomer of 1,2-propanediol to be used can be obtained by asymmetric hydrogenation of an acetol according to the method described in JP-63-316744.

The reaction of the optically active isomer of 1,2-propanediol and the acid halide of formula (V) is preferably carried out in an appropriate solvent in the presence of a base such as a tertiary amine. Examples of the solvent to be used include toluene, chlorobenzene, dichloromethane, dichloroethane, tetrahydrofuran, and diisopropyl ether. Examples of the tertiary amine to be used include triethylamine, pyridine, and dimethylaniline. As preferred reaction operations, a solution of the acid halide of formula (V) is added dropwise to a solution containing the optically active isomer of 1,2-propanediol and the base at a temperature of from −15° C. to 25° C., particularly from 5° C. to 15° C. over a period of from 1 to 10 hours, and the mixture is stirred at room temperature for an additional 5 to 20 hours.

After completion of the reaction, water in an amount of from ¼ to 1, preferably from ⅓ to ½ by volume of the solvent used is added to the reaction mixture. After heating at 70° C. to 80° C., an aqueous layer is separated out, and an oily layer is concentrated, whereby the optically active 1-acyloxy-2-propanol of formula (II) can be isolated. Furthermore, in the case of using, as the reaction solvent, a water-soluble solvent such as tetrahydrofuran or dioxane, the optically active isomer of 1-acyloxy-2-propanol (II) can be isolated by substituting the solvent with a solvent such as toluene or chlorobenzene and then conducting the isolation procedures as described above, or by filtering off a salt of the tertiary amine precipitated and concentrating the filtrate.

Since the optical purity of the desired compound, 2-(tetrahydropyran-2-yloxy)-1-propanol of formula (I) is greatly influenced by the optical purity of the starting optically active isomer of 1-acyloxy-2-propanol of formula (II), it is preferable to use a material with high optical purity as the starting material (II). The optical purity of the optically active isomer of 1-acyloxy-2-propanol of formula (II) can be improved by recrystallization from a solvent such as toluene, chlorobenzene, dichloromethane, dichloroethane, tetrahydrofuran, and diisopropyl ether.

This invention is described in more detail with reference to Examples, but it should not be construed to be limited thereto.

EXAMPLE 1

(1) Synthesis of 2-(R)-1-p-Nitrobenzoyloxy-2-propanol 500 g (6.58 mole) of 2-(R)-1,2-propanediol (optical purity: 92 %ee) and 732 g (7.24 mole) of triethylamine were dissolved in 5 liters of toluene, and 3.5 liters of a solution of 1282 g (6.9 mole) of p-nitrobenzoic acid chloride in toluene was added dropwise thereto over a period of 4 hours at the liquid temperature of not higher than 5° C. The mixture was reacted at room temperature for 15 hours with stirring, and 2.5 liters of water was added thereto, followed by stirring the mixture at 70° C. to 80° C. for an additional 30 minutes. After separating out an aqueous layer, the toluene was distilled off in vacuo (20 mmHg), the residue was left to stand at 0° C. for 15 hours, and precipitated crystals were collected by filtration.

The crystals were dried in vacuo (20 mmHg) at 50° C. for 5 hours to obtain 1125 g of 2-(R)-1-p-nitrobenzoyloxy-2-propanol (Compound II-1) (percent yield: 76%).

Measurement of Optical Purity 100 mg of Compound II-1 and 104 mg of (R)—(+)-α-methoxy-α-trifluoromethylphenylacetic acid were dissolved in 10 ml of dichloromethane, and 100 mg of 4-dimethylaminopyridine and 91.5 mg of dicyclohexylcarbodiimide were successively added to the solution. The mixture was then stirred for 15 hours at room temperature. After filtering off solids precipitated, the filtrate was analyzed by means of high performace liquid chromatography (HPLC). As a result, Compound II-1 was found to have an optical purity of 99.8 %ee.

$[\alpha]_D^{25} -18.2°$ (c=1, methanol).

Conditions of High Performance Liquid Chromatography

Column: Develosil® 100-3, 0.4 mmφ×25 cm.
Eluent: Hexane/Diethyl Ether=9/1. Flow Velocity =1 ml/min.
Detector: UV 254 nm (Model L-4000, manufactured by Hitachi, Ltd.). Pump (Model L-6000, manufatured by Hitachi, Ltd.).

$^1$H-NMR (CDCl$_3$): δppm 1.30 (d, 3H), 2.10 (s, 1H), 4.25 (m, 1H), 4.35 (dd, 2H), 8.20–8.30 (m, 4H).

(2) Synthesis of 2-(R)-2-(Tetrahydropyran-2-yloxy)-1-propanol (Compound I)

A 10-liter four-necked flask was charged with 966 g (4.293 mole) of 2-(R)-1-p-nitrobenzoyloxy-2-propanol, 38.6 g (0.165 mole) of camphor-10-sulfonic acid, and 4.5 liters of toluene, and a mixed solution of 396.7 g (4.72 mole) of 3,4-dihydro-2H-pyran and 500 ml of toluene were added dropwise to the mixture over a period of 2 hours in a nitrogen atmosphere at 10° C. to 15° C. After the dropwise addition, the resulting mixture was allowed to react with stirring at room temperature for an additional 3 hours. The reaction mixture was added dropwise to a mixed solution of 313 g (5.58 mole) of potassium hydroxide, 370 ml of water, and 1.8 liters of methanol over a period of 1 hour at a temperature not exceeding 25° C. After stirring for an additional 1 hour, a precipitate was filtered off, and the filtrate was separated into a toluene layer and an aqueous layer. After removing methanol at 40° C. in vacuo (10 mmHg), the aqueous layer was extracted twice with 1 liter of toluene. The extract was mixed with the toluene layer, and the solvent was distilled off to obtain 834 g of crude Compound I. Subsequently, the crude Compound I was distilled by means of a Claisen distillation apparatus to obtain 566 g of Compound I. As a result of the HPLC analysis, it was found to have a purity of 97.5%.

$^1$H-NMR (CDCl$_3$): δppm (diastereomer mixture) 1.14 (d, 1.5H), 1.22 (d, 1.5H), 1.56 (m, 4H), 1.77–1.86 (m, 2H), 3.44–3.61 (m, 3H), 3.82–4.08 (m, 2H), 4.55 (m, 0.5H), 4.73 (m, 0.5H).

IR: 3430 cm$^{-1}$, 1140 cm$^{-1}$.
Mass 129 (M—CH$_2$OH), 101 (M-CH$_3$CHCH$_2$OH)

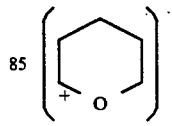

Measurement of Optical Purity of Compound I 20 g of Compound I and 2.9 g of D-camphor-10-sulfonic acid were added to 10 ml of water, and the mixture was stirred at room temperature for 15 hours, followed by extracting twice with 50 ml of methylene chloride. The extract was dried over anhydrous magnesium sulfate, and the solvent was then distilled off. The residue was distilled by means of a Claisen distillation apparatus to obtain 5 g of 2-(R)-1,2-propanediol.

10 mg of 2-(R)-1,2-propanediol, 100 mg of (R)-α-methoxy-α-trifluoromethylphenylacetic acid, 90 mg of dicyclohexylcarbodiimide, and 5 mg of 4-methylaminopyridine were dissolved in 2 ml of methylene chloride, and the mixture was stirred at room temperature for 15 minutes, followed by filtering off insoluble matters. The filtrate was analyzed by HPLC. As a result, the resulting Compound I was found to be substantially optically pure such that the optical purity was 99.8 %ee.

EXAMPLE 2

2 g (26.3 mmole) of 2-(R)-1,2-propanediol and 15 ml of pyridine were charged into a 100 cc container whose atmosphere had been previously substituted with nitrogen, and 4.97 g (26.8 mmole) of p-nitrobenzoic acid chloride was added to the mixture with ice-cooling. The resulting mixture was stirred at room temperature for 10 hours, and a precipitate was filtered off. After concentrating the filtrate in vacuo (100 mmHg) at room temperature, 30 ml of toluene was added to the residue, the mixture was heated (70° C.) to dissolve the residue and left to stand at 50° C. overnight. Precipitated crystals were collected and dried to obtain 3.6 g of 2-(R)-1-p-nitrobenzoyloxy-2-propanol (Compound II-1) (percent yield: 66%). Compound II-1 obtained herein was found to have an optical purity of 99.6 %ee.

Compound I was then obtained using Compound II-1 as in the same manner as in Example 1-(2).

EXAMPLE 3

40 g (0.526 mole) of 2-(R)-1,2-propanediol and 53.5 g (0.53 mole) of trimethylamine were charged into a container whose atmosphere had been previously substituted with nitrogen, and a solution of 102.4 g (0.52 mole) of p-nitrobenzoic acid chloride dissolved in 15 ml of tetrahydrofuran was added dropwise with ice-cooling over a period of about 7 hours. After the dropwise addition, the mixture was stirred at room temperature for 7 hours, and 200 ml of water and 150 ml of toluene were added thereto. After removing an aqueous layer, the toluene layer was concentrated at 40° C. in vacuo (20 mmHg) to obtain 126 g of a crude product. The crude product was dissolved in 380 ml of toluene under heating, and the same procedure as in Example 2 was followed to obtain 66 g of Compound II-1 (percent yield 66%). Compound II-1 obtained was found to have an optical purity of 99.6 %ee.

Compound I was then obtained using Compound II-1 in the same manner as in Example 1-(2).

EXAMPLE 4

14.8 g (0.2 mole) of 2-(R)-1,2-propanediol and 23 g (0.22 mole) of triethylamine were dissolved in 150 ml of toluene, and a solution of 43.1 g (0.2 mole) of p-bronobenzoic acid chloride dissolved in 50 ml of toluene was added dropwise thereto with ice-cooling (5° C. to 7° C.) over a period of 5 hours. The mixture was stirred at room temperature for an additional 10 hours, and 50 ml of water was added thereto. The resulting mixture was heated to 70° C. to form a homogeneous solution, followed by liquid separation. The toluene layer was left to stand at −5° C. overnight. Precipitated crystals were collected and dried to obtain 2-(R)-1-p-bromobenzoyloxy-2-propanol (Compound II-2) (percent yield: 71.1%).

$^1$H-NMR (CDCL$_3$): δppm 1.29 (d, 3H), 4:19 (m, 2H), 4.34 (m, 1H), 7.57-7.93 (m, 4H).

Compound II-2 obtained was found to have an optical purity of 99.1 %ee.

Compound I was then obtained using Compound II-2 in the same manner as in Example 1-(2).

According to this invention, optically active 2-(tetrahydropyran-2-yloxy)-1-propanol which is an intermediate for synthesis of pyridobenzoxazine derivatives useful as a synthetic antibacterial agent, especially 2-(R)-(tetrahydropyran-2-yloxy)-1-propanol as an intermediate for synthesis of an (S) isomer of ofloxacin, can be advantageously produced economically and industrially.

While the invention has been described in detail with reference to specific embodiments thereof, it will be apparent to one skilled in the art that various changes and modifications can be made therein without departing from the spirit and scope thereof.

What is claimed is:

1. A process for production of an optically active isomer of 2-(tetrahydropyran-2-yloxy)-1-propanol represented by formula (I):

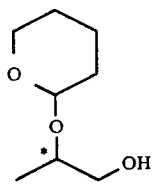

(I)

which comprises reacting an optically active isomer of a 1-acyloxy-2-propanol represented by formula (II):

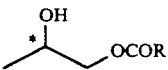

(II)

wherein R is a nitro or halogen substituted or unsubstituted phenyl group, with 3,4-dihydro-2H-pyran to obtain an optically active isomer of a 1-acyloxy-2-(tetrahydropyran-2-yloxy)propane represented by formula (III):

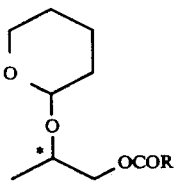

(III)

wherein R is as defined above, and hydrolyzing the compound (III) to eliminate the acyl group.

2. A process as in claim 1, wherein said active isomer of a 1-acyloxy-2-propanol represented by formula (II) is one obtainable by reacting an optically active isomer of 1,2-propanediol with an acid halide represented by formula (V):

RCOX      (V)

wherein X is a halogen atom, and R is as defined in claim 1.

3. A process as in claim 1, wherein R is selected from a phenyl group, a p-nitrophenyl group, a m-nitrophenyl group, an o-nitrophenyl group, a 2,4-dinitrophenyl group, a 2,6-dinitrophenyl group, a 3,4-dinitrophenyl group, a 3,5-dinitrophenyl group, a p-bromophenyl group, a m-bromophenyl group, an o-bromophenyl group, a p-iodophenyl group, a m-iodophenyl group, an o-iodophenyl group, a p-chlorophenyl group, a m-chlorophenyl group, and an o-chlorophenyl group.

4. A process as in claim 3, wherein R is a p-nitrophenyl group or a p-bromophenyl group.

* * * * *